United States Patent [19]

Villez

[11] Patent Number: 4,850,989
[45] Date of Patent: Jul. 25, 1989

[54] DIAPER WITH ELASTIC ON OUTER COVER

[75] Inventor: Yves Villez, Linselles, France

[73] Assignee: Peaudouce, Linselles, France

[21] Appl. No.: 225,094

[22] Filed: Jul. 27, 1988

Related U.S. Application Data

[63] Continuation-in-part of Ser. No. 127,465, Dec. 2, 1987.

[30] Foreign Application Priority Data

Jul. 30, 1987 [FR] France .................. 87 10835

[51] Int. Cl.$^4$ ............................. A61F 13/16
[52] U.S. Cl. ................... 604/385.2; 604/358
[58] Field of Search ............ 604/385 A, 385 R, 358

[56] References Cited

U.S. PATENT DOCUMENTS

| | | | |
|---|---|---|---|
| 4,081,301 | 3/1978 | Buell | 156/164 |
| 4,353,762 | 10/1982 | Bouda | 156/164 |
| 4,578,071 | 3/1986 | Buell | 604/379 |
| 4,585,447 | 4/1986 | Karami | 604/385 A |
| 4,661,102 | 4/1987 | Shikata et al. | 604/385 A |

FOREIGN PATENT DOCUMENTS

| | | |
|---|---|---|
| 0113976 | 7/1984 | European Pat. Off. . |
| 0270979 | 6/1988 | European Pat. Off. . |
| 3319043 | 11/1984 | Fed. Rep. of Germany . |
| 2388515 | 11/1978 | France . |

Primary Examiner—C. Fred Rosenbaum
Assistant Examiner—Mark O. Polutta
Attorney, Agent, or Firm—Owen, Wickersham & Erickson

[57] ABSTRACT

A diaper includes a flexible outer film impermeable to liquids and, on the inside surface of the outer film, longitudinal strips of adhesive and an absorbent pad. The pad has longitudinal edges set back from longitudinal edges of the outer film and transverse edges set back from transverse edges of the outer film. A flexible inner film permeable to liquids covers the inside surface of the outer film and the absorbent pad. It is adhesively bonded to the outer film in the area of contact between the films around the pad. Longitudinal elastic members are adhesively bonded while under tension to the outside surface of the outer film, along a central part of its longitudinal edge portions. The diaper also includes attachment means for fastening it around the body of the wearer and two flexible film tapes on the outside surface of the outer film over all its length and over a width that is greater than the width of the elastic members. These tapes enclose the elastic members.

9 Claims, 3 Drawing Sheets

DIAPER WITH ELASTIC ON OUTER COVER

This application is a continuation-in-part of application Ser. No. 127,465 filed Dec. 2, 1987.

BACKGROUND OF THE INVENTION

1. Field of the Invention

The present invention concerns a diaper comrising a flexible outer film impermeable to liquids, longitudinal strips of adhesive on an inside surface of said outer film, an absorbent pad on said inside surface of said outer film having longitudinal edges set back from longitudinal edges of said outer film and transverse edges set back from transverse edges of said outer film, a flexible inner film permeable to liquids covering said inside surface of said outer film and said absorbent pad thereon and adhesively bonded to said outer film in the area of contact between said films around said pad, longitudinal elastic members adhesively bonded while tensioned onto the outside surface of said outer film along a median part of its longitudinal edge portions, and attachment means for fastening the diaper around the body of the wearer.

The invention also concerns a method for continuous manufacture of such diapers.

2. Description of the Prior Art

The known method for continuous manufacture of diapers of the above-defined type consists in the steps of:

- unwinding a continuous strip of film impermeable to liquids,
- unwinding continuous elastic members, applying adhesive to said elastic members at intervals so as to obtain adhesive coated sections separated by sections not coated with adhesive, and applying said elastic members while tensioned to the upper surface of the impermeable film between lines of adhesive near the two longitudinal edge portions of the film, so as to adhesively bond the elastic members at successive spaced sections of the impermeable film,
- placing successively onto the upper surface of the impermeable film fitted with the elastic members individual absorbent pads having a width less than the width of the film so that the successive pads are placed on the film in the areas where the elastic members adhere to the latter and are spaced from each other in the direction of the length of the impermeable film,
- unwinding a continuous strip of film permeable to liquids having the same width as said impermeable film, applying adhesive to said permeable film on one side thereof and applying said adhesive coated side thereof to the upper surface of the impermeable film previously fitted with the elastic members and absorbent pads, and
- cutting successively in the transverse direction the two films and the tensioned elastic members, between the spaced consecutive pads, that is to say in the sections of the elastic members that are not coated with adhesive.

On making the transverse cuts which produce the individual diapers the initially continuous and tensioned elastic members are cut so that the parts of the elastic members disposed on each diaper on either side of the adhesive coated sections, adhering to the impermeable film, contract (i.e. relax), whereas the adhesive coated sections adhering to the outer film contract with said film to confer on the latter, in the crotch area of the diaper, the elasticity required to ensure a good fit to the body of the wearer and a good seal.

However, to enable relaxation of the parts of the elastic members not coated with adhesive on such cutting, it is also necessary to prevents these parts adhering to the adhesive coated permeable film. This is why until now areas not coated with adhesive have been provided, when applying adhesive to the permeable film, at the locations of the sections of the elastic members not coated with adhesive prior to cutting.

This produces in the area of the diaper between the spaced transverse edges of the absorbent pad and the permeable and impermeable films "tunnels" extending between the two films from the transverse edges of the pad to the transverse edges of the film, so that the space between the two films and containing the absorbent pad communicates with the exterior. These "tunnels" not only promote the escape to the exterior, by virtue of a draining effect, of urine absorbed by the pad, but also enable the material of the pad to escape to the exterior. This is the case, for example, with absorbent pads made from defibered cellulose pulp, and in particular with pads containing granular superabsorbent material which, although generally incorporated into some other material, such as defibered cellulose pulp, for example, is often readily detached from the absorbent pad and can, by escaping through these "tunnels", reach the exterior where, given its presentation as very small and light grains when dry, it can have unwanted or even harmful effects for the wearer.

French patent application No. 86 16 844 teaches the use of longitudinal tapes on the inside surface of the impermeable film of the diaper at the location of the elastic members so as to define "tunnels" into which the material of the absorbent pad placed over these ribbons cannot enter because the tunnels are only open at the transverse edges of the diaper.

It also teaches making the tapes forming the tunnels from a material impermeable to liquids so as to avoid any migration of liquid through these tunnels which are therefore isolated.

An object of the present invention is a diaper of the above-defined type in which the risk of the material of the absorbent pad escaping to the exterior is prevented with certainty. Another object of the invention is a diaper of the above-defined type in which the escape to the exterior at the longitudinal edges of the diaper of liquids absorbed by the pad of the diaper is prevented or at least strongly reduced. A further object of the invention is a diaper in which the risk of liquid escaping from the lateral (longitudinal) edges of the absorbent pad is prevented or at least strongly reduced.

A final object of the invention is a method for continuous manufacture of such diapers.

SUMMARY OF THE INVENTION

In one aspect, the present invention consists in a diaper comprising a flexible outer film impermeable to liquids, longitudinal strips of adhesive on an inside surface of said outer film, an absorbent pad on said inside surface of said outer film having longitudinal edges set back from longitudinal edges of said outer film and transverse edges set back from transverse edges of said outer film, a flexible inner film permeable to liquids covering said inside surface of said outer film and said absorbent pad thereon and adhesively bonded to said outer film in the area of contact between said films around said pad, longitudinal elastic members adhesively bonded while tensioned onto the outside surface of said outer film along a central part of its longitudinal edge portions, attachment means for fastening the diaper around the body of the wearer, and two flexible film tapes on said outside surface of said outer film over all the length thereof and over a width greater than the width of said elastic members, enclosing said elastic members.

It has been discovered that the problem as explained can be overcome by placing the longitudinal tapes and the plastic members that they cover not on the inside surface of the impermeable film but rather on its outside surface, in substantially the same transverse position. In this way perfect isolation of the tunnels is obtained, as neither liquids nor any granular material included in the absorbent pad can enter them.

The tapes may be made from a non-woven fabric or from an impermeable material given that in this embodiment the impermeability to liquids in the absorbent pad results no longer from the material of the tapes but from that of the impermeable outer film. The choice of the material for the tapes therefore depends essentially on esthetic considerations or on considerations of surface state for contact with the exterior of the diaper.

The elastic members used may each comprise an elastic material strap. They may equally well comprise a plurality of parallel individual strands.

In a preferred embodiment the elastic members are fixed in the tensioned state by adhesive bonding their middle portion, the unattached front and rear ends being free of tension and retracted inside tunnels formed by the tapes.

The elastic members are preferably arranged in a straight line. It will be noted, however, that it is perfectly feasible to consider the use of elastic members disposed on a curvilinear path, for example following the edge of the diaper or that of the absorbent pad.

It is also feasible to consider the use of elastic members adhesively bonded over all of their length but not having the same elasticity characteristics in all sections. It is therefore possible to use elastic members exerting traction in their middle portion so as to form puckers in the crotch area of the diaper while the end portions of the same elastic members are adhesively bonded to the outside surface of the impermeable film and do not exert any traction on the latter.

In another aspect, the present invention consists in a method for continuously manufacturing diapers, comprising the steps of:
  unwinding two spaced continuous tapes of film;
  applying continuously to an upper surface of said tapes continuous strip or strand elastic members to parts at least of which adhesive has been previously applied and which are stretched to an appropriate tension;
  unwinding a continuous strip of film impermeable to liquids;
  applying continuously to a lower surface of said continuous impermeable film said two continuous tapes and said elastic members adhesively bonded to them;
  applying continuously transversely spaced longitudinal strips of adhesive to an upper surface of said continuous impermeable film;
  placing absorbent pads on said upper surface of said continuous impermeable film;
  unwinding a continuous strip of film permeable to liquids having substantially the same width as said continuous impermeable film and applying said permeable film to an upper surface of said impermeable film so that said permeable film adheres to said impermeable film all around said absorbent pads; and
  cutting the resulting assembly transversely between consecutive absorbent pads.

During cutting, the end parts of the elastic members applied when tensioned that are not coated with adhesive can retract into the tunnels formed by the tapes adhesively bonded to the lower and outside surface of the impermeable film.

The invention will be better understood from a specific embodiment to be described by way of non-limiting example only with reference to the appended drawings.

DESCRIPTION OF THE PREFERRED EMBODIMENT

Figure 1:
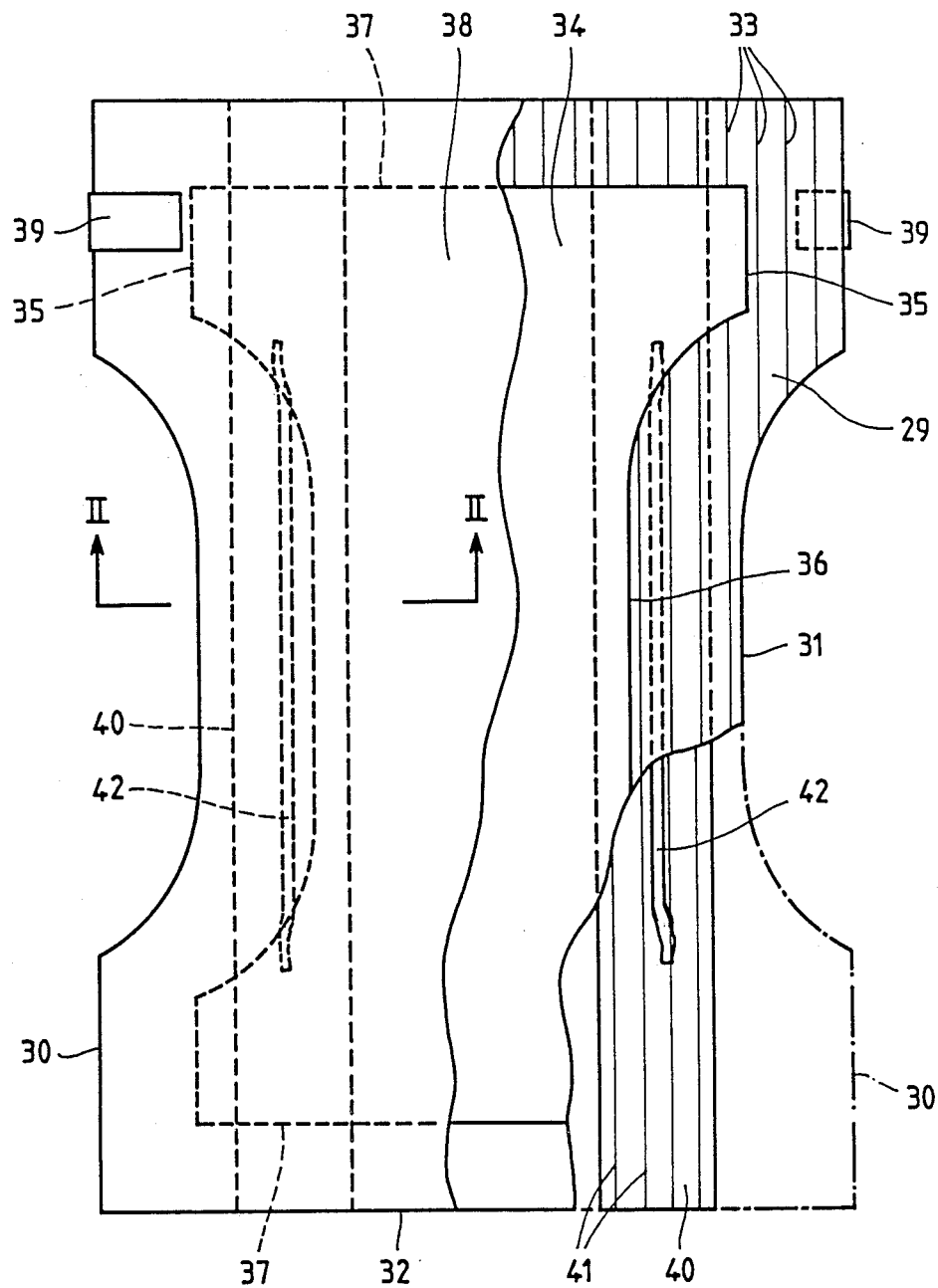
FIG. 1 shows the inside surface of a diaper in accordance with the invention shown flat, with the elastic members tensioned, the figure being partially cut away at two places to show the internal structure of the diaper.
Figure 2:
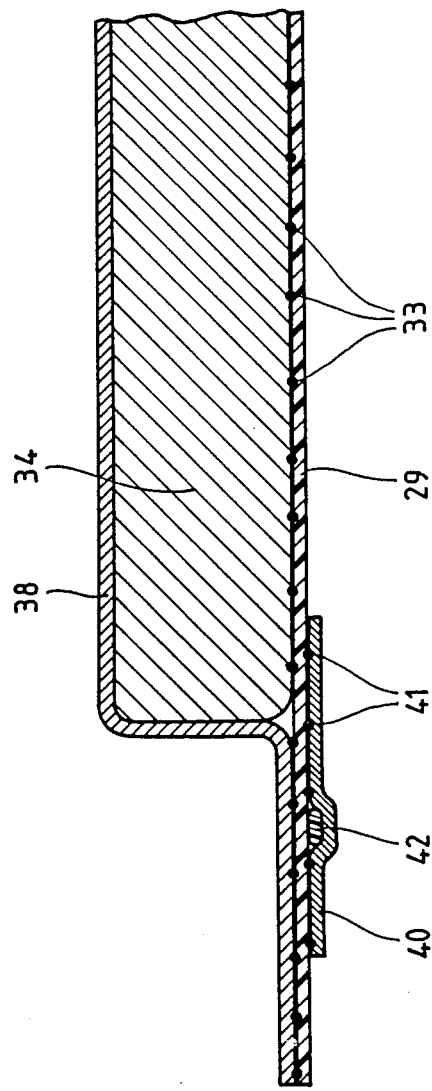
FIG. 2 is a cross-section to a larger scale on the line II—II in FIG. 1.

As shown in FIGS. 1 and 2, the diaper comprises a flexible outer film 29 impermeable to liquids, for example a film of plastics material such as polyethylene, having a generally rectangular shape with two longitudinal edges 30 each having a central cut-out 31, and two straight transverse edges 32. The film 29 carries on its inside surface, visible in FIG. 1, a multitude of spaced longitudinal lines of adhesive 33.

An absorbent pad 34 which is generally hourglass-shaped has two longitudinal edges 35 each having a central cut-out 36 and two straight transverse edges 37. It is fixed to the inside surface of the film 29 so that its longitudinal edges 35 and transverse edges 37 are set back from the longitudinal edges 30 and transverse edges 32 of the film 29.

The absorbent pad 37 may be made from defibered cellulose pulp, for example, optionally containing granular superabsorbent material. The pad 37 is fixed to the film 29 by the lines of adhesive 33.

The whole of the film 29 is covered on the inside surface carrying the absorbent pad 37 with a film 38 permeable to liquids, a non-woven fabric film, for example. The film 38 may be provided on the side facing towards the film 29 with a coating of adhesive so that the film 38 adheres at least to the film 29 all around the perimeter of the absorbent pad 34. This adhesive may be applied over all the surface of the film 38, in which case the latter adheres also to the absorbent pad 34, or in a closed frame shape around an opening that can be of rectangular shape, for example, or the same shape as the absorbent pad 34.

Adhesive attachment members 39 of known type are fixed to the two longitudinal edge portions 30 of the diaper at the rear for attaching the diaper around the waist of the wearer.

A tape 40 made from a flexible film material, for example a non-woven material or coated or uncoated paper or a plastics material, is fixed to the outside surface of the film 29 over the whole of its length, as can be seen in FIG. 2 in particular. The fixing is done by longitudinal lines of adhesive 41. Between the tape 40 and the impermeable film 29 is an elastic member 42 in the form of an elastic material strap adhesively bonded while tensioned to the inside surface of the longitudinal tape 40. The elastic member 42 is coated with adhesive only in the central area which corresponds substantially to the cut-out 36 of the absorbent pad 34 fixed to the inside surface of the impermeable film 29. The end portions of the elastic member 42 are not coated with adhesive, however. On making the transverse cuts which define the individual diapers, the elastic members 42 are therefore cut in line with the transverse edges 32 of the impermeable film 29. The tensioned ends of the elastic members 42 that are not coated with adhesive retract inside the tunnel formed between the longitudinal tape 40 and the outside surface of the impermeable film 29, as shown in FIG. 1.

It will be noted that each elastic member 42 is placed so as to be slightly outside the edge of the cut-out 36 of the absorbent pad 34.

Because the elastic members 42 and the longitudinal tapes 40 are outside the impermeable film 29, it is clear that the material of the absorbent pad 34 cannot under any circumstances enter the tunnel defined by the tapes 40 and escape to the exterior through these tunnels, irrespective of the material from which the tapes 40 are made.

Figure 3:
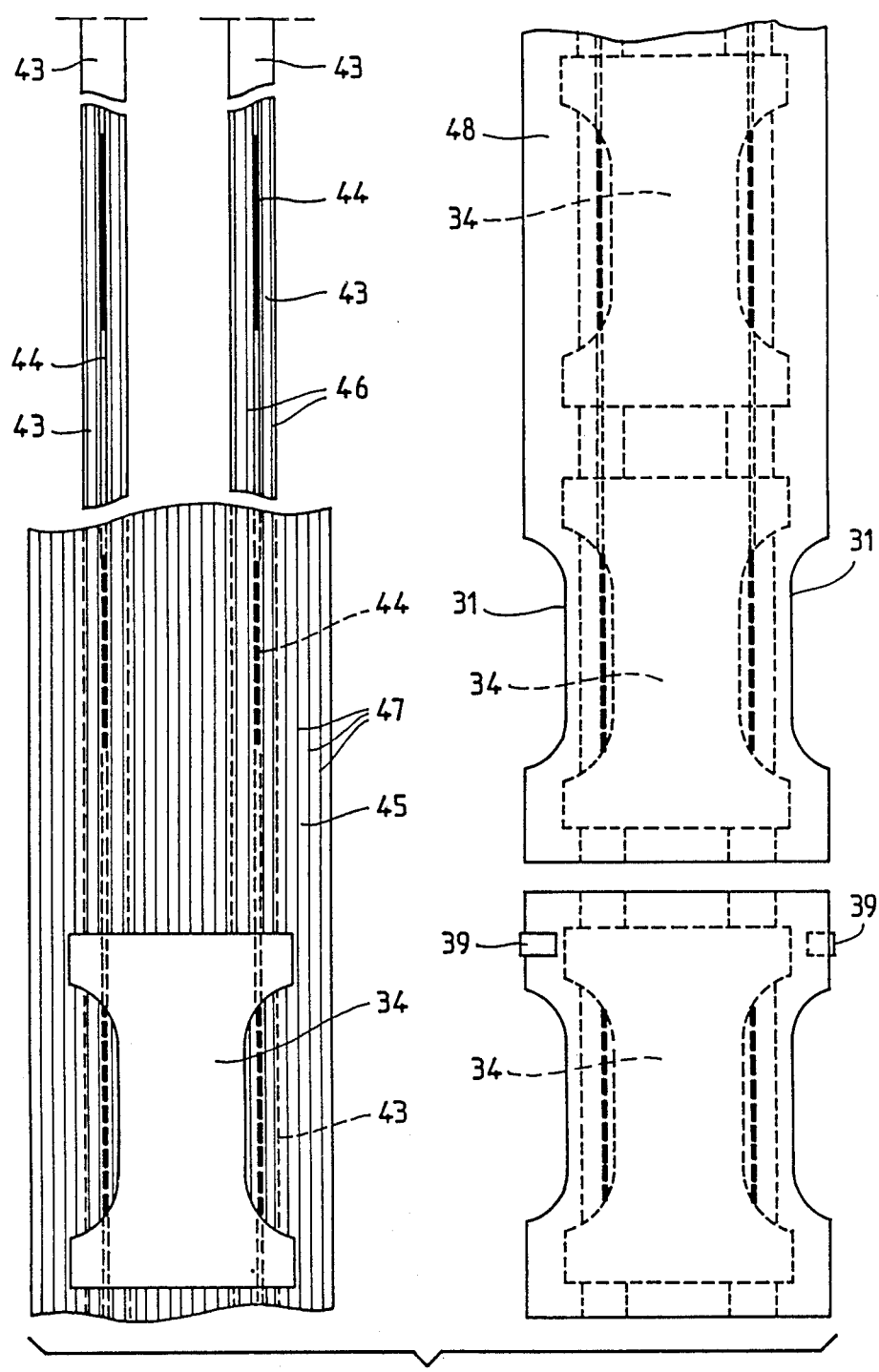
FIG. 3 shows the various main steps in continuous manufacture of diapers as shown in FIGS. 1 and 2.

There will now be described with reference to FIG. 3 a preferred method for continuous manufacture of diapers as shown in FIGS. 1 and 2.

First, two tapes 43 of film are unwound continuously with a distance between them which is the same as the distance they are to have between them in the finished diaper. To the upper surface of these two tapes are continuously applied elastic members in the form of continuous straps 44 or continuous individual parallel strands. These continuous elastic members have previously been coated with adhesive, in successive sections, for example, and they are placed under constant tension and fixed only in alternating sections. In alternative embodiments consideration may be given to continuous adhesive bonding with variation in the tension of the continuous elastic member.

Following this operation there is unwound continuously a strip of film 45 impermeable to liquids to form the impermeable film 29 of the diaper and the two continuous tapes 43 provided with the adhesively bonded elastic members 44 as already described are applied continuously to the lower surface of the continuous film 45. This fixing is done by means of lines of adhesive 46 applied continuously and directly to the tapes 43 or to the lower surface of the continuous film 45, for example. A multitude of longitudinal lines of adhesive 47 are applied to the upper surface of the continuous impermeable film 45 and then the absorbent pads 34 are placed, having been previously cut to a shape similar to that of an hourglass. A continuous strip of flexible film 48 permeable to liquids is then unwound. It is the same width as the film 45 and it is adhesively bonded to the upper surface of the film 45 above the pads 34.

Two side cut-outs 31 are cut into the two films 45 and 48, substantially in the central are of each pad 34. After fixing the adhesive attachments 39 at the appropriate locations, the resulting assembly is cut transversely which causes the end parts of the continuous elastic members 44, the parts not coated with adhesive, to retract.

There is claimed:

1. Diaper comprising a flexible outer film impermeable to liquids, longitudinal strips of adhesive on an inside surface of said outer film, an absorbent pad on said inside surface of said outer film having longitudinal edges set back from longitudinal edges of said outer film and transverse edges set back from transverse edges of said outer film, a flexible inner film permeable to liquids covering said inside surface of said outer film and said absorbent pad thereon and adhesively bonded to said outer film in the area of contact between said films around said pad, longitudinal elastic members adhesively bonded while tensioned onto the outside surface of said outer film along a central part of its longitudinal edge portions, attachment means for fastening the diaper around the body of the wearer, and two flexible film tapes on said outside surface of said outer film over all the length thereof and over a width greater than the width of said elastic members, enclosing said elastic members.

2. Diaper according to claim 1, wherein said tapes are adhesively bonded to said outside surface of said outer film.

3. Diaper according to claim 1, wherein at least parts of the length of said elastic members are adhesively bonded to an inside surface of said tapes.

4. Diaper according to claim 1, wherein said tapes are made from a non-woven fabric.

5. Diaper according to claim 1, wherein said absorbent pad contains a granular superabsorbent material.

6. Diaper according to claim 1, wherein each elastic member is an elastic strap.

7. Diaper according to claim 1, wherein each elastic member comprises parallel strands.

8. Diaper according to claim 1, wherein central parts of said elastic members are adhesively bonded to said outer film while tensioned and their front and back ends are not tensioned and retract under said tapes.

9. Diaper according to claim 1, wherein said elastic members are straight.

* * * * *